US008652261B2

(12) United States Patent
O'Connor

(10) Patent No.: US 8,652,261 B2
(45) Date of Patent: Feb. 18, 2014

(54) PROCESS FOR DISSOLVING CELLULOSE-CONTAINING BIOMASS MATERIAL IN AN IONIC LIQUID MEDIUM

(75) Inventor: Paul O'Connor, Hoevelaken (NL)

(73) Assignee: KiOR, Inc., Pasadena, TX (US)

( * ) Notice: Subject to any disclaimer, the term of this patent is extended or adjusted under 35 U.S.C. 154(b) by 0 days.

(21) Appl. No.: 13/391,752

(22) PCT Filed: Sep. 1, 2010

(86) PCT No.: PCT/IB2010/002355
§ 371 (c)(1),
(2), (4) Date: Aug. 3, 2012

(87) PCT Pub. No.: WO2011/027220
PCT Pub. Date: Mar. 10, 2011

(65) Prior Publication Data
US 2012/0291773 A1 Nov. 22, 2012

Related U.S. Application Data

(60) Provisional application No. 61/238,725, filed on Sep. 1, 2009.

(51) Int. Cl.
*C08H 8/00* (2010.01)

(52) U.S. Cl.
USPC .......................................................... 127/37

(58) Field of Classification Search
None
See application file for complete search history.

(56) References Cited

U.S. PATENT DOCUMENTS

| 5,410,034 | A | 4/1995 | Isogai et al. | |
|---|---|---|---|---|
| 6,824,599 | B2 * | 11/2004 | Swatloski et al. | 106/163.01 |
| 7,503,981 | B2 * | 3/2009 | Wyman et al. | 127/37 |
| 2007/0161095 | A1 | 7/2007 | Gurin | |
| 2008/0185112 | A1 | 8/2008 | Argyropoulos | |
| 2008/0190013 | A1 | 8/2008 | Argyropoulos | |
| 2008/0227162 | A1 | 9/2008 | Varanasi | |
| 2008/0227972 | A1 | 9/2008 | Yamaguchi | |
| 2009/0011473 | A1 | 1/2009 | Varanasi | |
| 2010/0163018 | A1 | 7/2010 | Gifford | |

FOREIGN PATENT DOCUMENTS

| DE | 102004031025 | 12/2005 |
|---|---|---|
| EP | 2006354 | 12/2008 |
| EP | 2033974 | 3/2009 |
| GB | 2451046 | 1/2009 |
| WO | WO/03029329 | 4/2003 |
| WO | WO/2005017252 | 2/2005 |
| WO | WO/2006119357 | 11/2006 |
| WO | WO/2007112090 | 10/2007 |
| WO | WO/2008043837 | 4/2008 |
| WO | WO/2008098036 | 8/2008 |
| WO | WO/2008112291 | 9/2008 |
| WO | WO/2008119770 | 10/2008 |
| WO | WO/2010100126 | 9/2010 |
| WO | WO/2011027223 | 3/2011 |
| WO | WO/2011028776 | 3/2011 |
| WO | WO/2011028783 | 3/2011 |
| WO | WO/2011028788 | 3/2011 |

OTHER PUBLICATIONS

Fischer, Unconventional Dissolution and Derivatization of Cellulose, Lenzinger Berichte, 83 (2004) 71-78.*
Bridgwater A.V. "Catalysis in thermal biomass conversion" Applied Catalysis, A: general, Elsevier Science, Amsterdam NL, 1994, 116, 5-47.
Cuissinat et al. "Swelling and dissolution of cellulose. Part IV: Free floating cotton and wood fibres in ionic liquids." Carbohydrate Polymers, Applied Science Publishers, Ltd. Barking, GB, 2008, 72, 590-596.
Duchemin B.J. e al. "All-cellulose composites by partial dissolution in the ionic liquid 1-butyl-3-methylimidazolium chloride" Composites Part A: Applied Science and manufacturing, Elsevier Science Publishers, Amsterdam, NL, 2009, 40, 2031-2037.
Fischer S. et al. "The behaviour of cellulose in hydrated melts of the composition LiX.nH2O (X=I-, NO3-, CH3COO-, C1O4)" Cellulose, Kluwer Academic Publishers, 1999, 6, 213-219.
Fischer S. et al. "Evaluation of molten inorganic salt hydrates as reaction medium for the derivatization of cellulose" Cellulose, Kluwer Academic Publishers, 2002, 9, 293-300.
Fischer S. et al. "Inorganic molten slats as solvents for cellulose" Cellulose, 2003, 227-236.
Fort et al. "Can ionic liquids dissolve wood? Processing and analysis of lignocellulosic materials with 1-n-butyl-3-methylimidazolium chloride", Green Chemistry, Royal Society of Chemistry, Cambridge, GB, 2007, 9, 63-69.
Heinze T. et al. "Unconventional methods in cellulose functionalization" Progress in Polymer Science, Pergamon Press, Oxford, GB, 2001, 26, 1689-1762.
Kilpelainen I et al. "Dissolution of wood in ionic liquids" J. Agric. Food Chem. 2007, 55, 9142-9148.
Li C. et al. "Comparison of dilute acid and ionic liquid pretreatment of switchgrass: Biomass recalcitrance, delignification and enzymatic saccharification", Bioresource Technology, Elsevier BV, GB, 2010, 101, 4900-4906.
Salanti A. et al. "Characterization of waterlogged wood by MMR and GPC techniques",.Microchemical Journal, 2010, 95, 345-352.
Schall C. et al. "Ionic liquid pretreatment of lignocellulosic for biofuels production", American Chemical Society, Abstract of paper at the National Meeting, American Chemical Society, US, 2008, 236.
Sheldrake G.N. et al. "Dicationic molten salts (ionic liquids) as re-usable media for the controlled pyrolysis of cellulose to anhydrosugars", Green Chemistry, Royal Society of Chemistry, Cambridge, GB, 2007, 9, 1044-1046.
Singh, S. et al. "Visualization of biomass solubilization and cellulose regeneration during ionic liquid pretreatment of switchgrass" Biotechnology and Bioengineering, 2009, 104, 68-75.
Takashi Hosoya et al. "Influence of inorganic matter on wood pyrolysis at gasification temperature", Journal of Wood Science: Official Journal of the Japan Wood Research Society, Springer Verlag, TO, 2007, 53, 351-357.
International Search Report in International Application No. PCT/IB2010/002355 mailed Jul. 2, 2011.

* cited by examiner

*Primary Examiner* — Melvin C Mayes
*Assistant Examiner* — Stefanie Cohen
(74) *Attorney, Agent, or Firm* — Jennifer A. Camacho; Natalie Salem; Greenberg Traurig, LLP

(57) ABSTRACT

A process is disclosed for dissolving the cellulose component if a cellulose-containing biomass material in an Ionic Liquid medium. The biomass material contains minerals. At least part of the minerals are removed prior to contacting the biomass material with the Ionic Liquid medium. The Ionic Liquid medium preferably is an inorganic molten salt hydrate.

15 Claims, No Drawings

PROCESS FOR DISSOLVING CELLULOSE-CONTAINING BIOMASS MATERIAL IN AN IONIC LIQUID MEDIUM

RELATED APPLICATIONS

This application is a National Phase application of International Application No. PCT/IB2010/002355 filed Sep. 1, 2010, which claims benefit of and priority to U.S. provisional patent application Ser. No. 61/238,725, filed Sep. 1, 2009, the content of each of the foregoing applications is incorporated herein by reference in its entirety.

BACKGROUND OF THE INVENTION

1. Field of the Invention

The invention relates generally to a process for dissolving cellulose from a biomass material in an Ionic Liquid medium, and more particularly to integrating the dissolution process into a process in which cellulose is regenerated, derivatized, or converted.

2. Description of the Related Art

It has been known to dissolve cellulose in Ionic Liquids. S. Fischer et al., "*Inorganic molten salts as solvents for cellulose*", Cellulose 10: 227-236, 2003, discloses the use of various molten salt systems as solvent media for cellulose. Upon dissolution, cellulose can be derivatized by carboxymethylation or acetylation. The starting material is pure cellulose.

Sheldrake and Schleck, "*Dicationic molten salts* (ionic liquids) *as re-usable media for the controlled pyrolysis of cellulose to anhydrosugars*", Green Chem 2007, pp 1044-1046, reports on low temperature pyrolysis of cellulose in ionic liquid media. The starting material is pure cellulose.

For commercially viable processes it is desirable to use lower grade sources of cellulose as the feedstock. However, lower grade cellulose sources, such as lignocellulosic biomass materials, inevitably contain minerals. These minerals can interact with the Ionic Liquid medium and change its solvent properties.

Thus, there is a need for a process in which the cellulose component of a biomass material comprising cellulose and minerals is dissolved in an Ionic Liquid medium.

BRIEF SUMMARY OF THE INVENTION

The present invention addresses these problems by providing a process for dissolving at least part of the cellulose component of a cellulose-containing biomass material in an Ionic Liquid medium, said process comprising the steps of:
 (i) providing a biomass material comprising cellulose and minerals;
 (ii) subjecting the biomass material to a demineralization treatment in which at least part of the minerals are removed from the biomass material;
 (iii) contacting the at least partially demineralized biomass material from step (ii) with an Ionic Liquid medium, thereby dissolving at least part of the cellulose component of the biomass material.

DETAILED DESCRIPTION OF THE INVENTION

The present invention relates to a process for dissolving at least part of the cellulose component of a cellulose-containing biomass material in an Ionic Liquid medium, said process comprising the steps of:
 (i) providing a biomass material comprising cellulose and minerals;
 (ii) subjecting the biomass material to a demineralization treatment in which at least part of the minerals are removed from the biomass material;
 (iii) contacting the at least partially demineralized biomass material from step (ii) with an Ionic Liquid medium, thereby dissolving at least part of the cellulose component of the biomass material.

The biomass material can be any cellulose-containing biomass material. For example, the biomass material can comprise aquatic biomass material, such as algae. Aquatic biomass material offers several advantages. Aquatic plants are more efficient than are land plants in converting solar energy into biomass material. In addition, many types of aquatic plants do not require a supply of fresh water, and in fact thrive in sea water or brackish water. On the other hand, aquatic biomass generally contains large amounts of water, which can be hard to remove. In particular micro-algae are difficult to separate from much of the water occluded in the plant cells. Many forms of Ionic Liquid media have a low tolerance for moisture.

Another drawback of aquatic biomass is the relatively high mineral content. Minerals interfere with the solvent properties of Ionic Liquid media in ways that are poorly understood, if understood at all.

Land-based plants generally contain cellulose in the form of lignocellulose, which is a natural composite of lignin and cellulose, generally further comprising hemicellulose. Some known Ionic Liquid media are capable of dissolving both cellulose and lignin. These media are naturally capable of dissolving the lignocellulose composite. Dissolved lignin can interfere with the further processing of dissolved cellulose. It is therefore often desirable to remove dissolved lignin from the Ionic Liquid medium, or to prevent lignin from becoming dissolved.

Many lignocellulosic biomass materials for example bagasse, contain large amounts of minerals. Other lignocellulosic materials, such as the sap wood part of a tree, contains relatively small amounts of minerals. In general, however, tree-based biomass feedstock comprises bark and leaves, which are both mineral-rich.

It is in general not possible to dissolve biomass material in an Ionic Liquid medium without introducing minerals in quantities large enough to interfere with the solvent properties of the Ionic Liquid medium.

In important aspect of the process of the present invention is the step of subjecting the biomass material to a demineralization step. This demineralization step preferably is carried out before contacting the biomass material with the Ionic Liquid medium. In the demineralization step at least part of the minerals are removed from the biomass material.

The demineralization step can comprise contacting the biomass material with a solvent for the minerals, that is, a material, usually a liquid, in which the minerals present in the biomass material readily dissolve. The demineralization step further comprises separating the solvent (in which at least part of the minerals are dissolved) from the biomass material.

It is advantageous to contact the biomass material with the solvent in the form of small particles, having a median particle size in the range of from 100 μm to 10 cm, preferably from 1000 μm to 3 cm. It is further advantageous to apply mechanical action while contacting the biomass material with the solvent. Examples of mechanical action include kneading, high shear mixing, wet milling, and the like.

In general step (ii) is carried out at a temperature in the range of from 25° C. to 200° C.

In one embodiment the biomass material is contacted with the solvent at a temperature in the range from ambient to just below the boiling point of the solvent.

In an alternate embodiment the biomass material is contacted with the solvent at a temperature above the boiling point of the solvent. In this embodiment this process step is carried out under pressure, for example in an autoclave.

In yet another embodiment the step of contacting the biomass is carried out under conditions of temperature and pressure at which the solvent is a super-critical fluid. Water is a super-critical fluid at temperatures above 374° C., corresponding to pressures above 22 MPa. Carbon dioxide is another example of a suitable solvent when in the form of a supercritical fluid. For $CO_2$ the critical point is at about 77° C. and about 7.4 MPa pressure.

Any solid/liquid separation technique can be used for separating the solvent from the partially demineralized biomass material. Examples include filtration, pressing, centrifugation, and the like.

For reasons of cost and safety, the solvent preferably is an aqueous liquid. The term aqueous liquid as used herein encompasses water, and aqueous solutions of materials that assist in dissolving minerals from biomass material. Examples of such assisting materials include acids and bases.

Step (ii) can comprise (a) swelling the biomass material in the solvent; and (b) removing at least part of the solvent by applying pressure to the swollen biomass material. Sub-step (b) can be carried out, for example, in a filter press or a kneader. It can be advantageous to repeat sub-steps (a) and (b) at once or several times. Repeating these steps results in removal of a greater portion of the minerals present in the biomass material; this gain is subject, however, to the law of diminishing returns.

The Ionic Liquid medium can comprise an organic cation. In particular dicationic organic Ionic Liquids are excellent solvents for cellulose and hemicellulose. Several organic Ionic Liquids have been reported in the literature as being capable of (partially) dissolving the lignin component of lignocellulosic materials. Organic Ionic Liquids also have major disadvantages, the most important ones being high cost, and limited temperature resistance. Many have the additional disadvantage that they are poor solvents for cellulose when contaminated with water.

Preferred Ionic Liquids are inorganic Ionic Liquids, in particular inorganic molten salt hydrates. As compared to organic Ionic Liquids, inorganic Ionic Liquids are more temperature stable, and have a lower cost. In addition, in particular the inorganic molten salt hydrates are effective solvents for cellulose even in the presence of water. In fact, as their name indicates, a certain amount of water needs to be present for these materials to function as Ionic Liquid media.

Inorganic Ionic Liquids have an inorganic anion. The anion can contain a halogen atom. Examples include halides, oxyhalides and hydroxyhalides, in particular chloride, oxychlorides, and hydroxychlorides. The anion can also be hydroxide; for example, the hydroxide of the Cu/ammonia complex is a suitable Ionic Liquid medium for use in the process of the present invention.

The molten salt hydrate further comprises a cation, in particular Zn, Ba, Ca, Li, Al, Cr, Fe, or Cu.

Mixtures of inorganic salts can also be used, in particular eutectic mixtures. In general, any salt or salt hydrate that is liquid at a temperature of 200° C. or below, and is capable of dissolving cellulose, is suitable as the Ionic Liquid medium in the process of the present invention.

Particularly preferred are the hydrates of $ZnCl_2$, in particular $ZnCl_2.4H_2O$.

In general, lignin is not soluble in inorganic molten salt hydrates. It has been found that these materials are nevertheless capable of dissolving the holocellulose (both cellulose and hemicellulose) component of the lignocellulose composite. Undissolved lignin can be easily removed from the inorganic molten salt hydrate, using such techniques as decantation, filtration and centrifugation. As the lignin component generally contains a significant portion of the minerals, this technique results in further removal of minerals.

Inorganic molten salt hydrates have the additional advantage of being able to dissolve cellulose in the presence of significant amounts of water. In fact, these materials need for a certain amount of water to be present in order for them to exhibit their optimum dissolution properties.

Yet another advantage of inorganic molten salt hydrates over organic Ionic Liquid media is the temperature resistance of the former. This is of particular interest when the dissolved cellulose is further processed at elevated temperatures. For example, the pyrolysis of cellulose requires temperatures in excess of 300° C., at which many organic Ionic Liquid media are thermally unstable.

Preferably the process comprises the further step (iv) of removing at least part of the dissolved cellulose. This step (iv) can comprise precipitation of the dissolved cellulose; derivatization of the dissolved cellulose, followed by precipitation of the cellulose derivative; or chemical conversion of the dissolved cellulose, preferably to a reaction product that is insoluble in the Ionic Liquid medium.

In one embodiment cellulose is regenerated from the solution by mixing the solution with a coagulant, or non-solvent, for cellulose. Examples of suitable non-solvents include water and the lower alcohols, in particular ethanol and methanol.

In an alternate embodiment the dissolved cellulose is derivatized in situ, for example to cellulose acetate. The term "derivatization" as used herein refers to any chemical reaction that changes the chemical nature of cellulose, while leaving the cellulose backbone structure in tact. The cellulose derivative may be insoluble in the Ionic Liquid medium, in which case it spontaneously precipitates from the solution. If the cellulose derivative is soluble in the Ionic Liquid medium it can be removed therefrom by mixing the Ionic Liquid medium with a non-solvent for the derivative. In general, water and the lower alcohols are suitable non-solvents.

In yet another embodiment dissolved cellulose is chemically converted to a reaction product that is insoluble in the Ionic Liquid medium. For example, cellulose can be hydrolyzed in solution to glucose. In turn, glucose can be converted, using a sequence of hydrogenation and dehydration steps, to isosorbide, which is insoluble in most Ionic Liquid media.

In a preferred embodiment the process comprises the additional step (v) of regenerating the Ionic Liquid medium obtained in step (iv). This additional regeneration step can comprise removing water from the Ionic Liquid medium. The regeneration step can comprise removing undissolved material from the Ionic Liquid medium.

The removal of water can generally be accomplished by distillation. For example, step (iv) may be carried out under increased pressure, at temperatures exceeding 100° C. By releasing the pressure while the temperature of the Ionic Liquid medium is maintained above 100° C., water is flashed off in a process sometimes referred to as flash-distillation.

After regeneration the Ionic Liquid medium may be recycled to step (iii) of the process. This feature is particularly useful if the process is conducted in continuous mode. It will be understood, however, that the process can be conducted in batch mode as well.

The invention claimed is:

1. A process for dissolving at least part of the cellulose component of a cellulose-containing biomass material, said process comprising the steps of:
   (i) providing a biomass material comprising cellulose and minerals;
   (ii) subjecting the biomass material to a demineralization treatment in which at least part of the minerals are removed from the biomass material; and
   (iii) contacting the at least partially demineralized biomass material from step (ii) with an Ionic Liquid medium, thereby dissolving at least part of the cellulose component of the biomass material, wherein the Ionic Liquid medium comprises a molten salt hydrate, and
   wherein the molten salt hydrate comprises a cation selected from the group consisting of Ba, Al, Cu, $Cu(NH_3)_x$ and Cr.

2. The process of claim 1 comprising the further step (iv) of removing at least part of the dissolved cellulose from the Ionic Liquid medium.

3. The process of claim 2 wherein step (iv) comprises mixing the Ionic Liquid medium with a coagulant to precipitate the dissolved cellulose, and recovering the precipitated cellulose; or wherein step (iv) comprises converting dissolved cellulose to a reaction product that is insoluble in the Ionic Liquid medium, and removing the reaction product from the Ionic Liquid medium.

4. The process of claim 3 wherein the cellulose is derivatized prior to precipitation.

5. The process of claim 2 comprising the further step (v) of regenerating the Ionic Liquid medium obtained in step (iv).

6. The process of claim 5 wherein step (v) comprises removing undissolved material from the Ionic Liquid medium.

7. The process of claim 5 wherein step (v) comprises removing excess water from the Ionic Liquid medium.

8. The process of claim 5 comprising the further step of recycling regenerated Ionic Liquid medium to step (iii).

9. The process of claim 8 wherein the process is a continuous process.

10. The process of claim 1 wherein the biomass material comprises an aquatic biomass material or a lignocellulosic material.

11. The process of claim 1 wherein step (ii) comprises: (a) contacting the biomass material with a solvent for the minerals; and (b) separating the solvent from the biomass material.

12. The process of claim 11 wherein the solvent is an aqueous liquid.

13. The process of claim 11 wherein the solvent comprises an acid or a base.

14. The process of claim 11 wherein step (ii) comprises: (a) swelling the biomass material in the solvent; and (b) removing at least part of the solvent by applying pressure to the biomass material and optionally repeating steps (ii)(a) and (ii)(b) at least once.

15. The process of claim 1 wherein step (ii) is carried out at a temperature in the range of from 25° C. to 200° C.

* * * * *